(12) United States Patent
Abe

(10) Patent No.: US 6,475,141 B2
(45) Date of Patent: Nov. 5, 2002

(54) ELECTRONIC ENDOSCOPE DEVICE USING SEPARATED AREA PHOTOMETRY

(75) Inventor: Kazunori Abe, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/891,346

(22) Filed: Jun. 27, 2001

(65) Prior Publication Data

US 2002/0004626 A1 Jan. 10, 2002

(30) Foreign Application Priority Data

Jun. 29, 2000 (JP) ........................................ 2000-196394
Jun. 29, 2000 (JP) ........................................ 2000-196395

(51) Int. Cl.[7] ................................................ A61B 1/00
(52) U.S. Cl. ............................. 600/180; 348/69; 348/72
(58) Field of Search ................................ 600/180, 181; 346/68–70, 72, 221, 229, 362; 362/4, 574

(56) References Cited

U.S. PATENT DOCUMENTS 4,868,645 A * 9/1989 Kobayashi .................. 348/69
5,959,670 A * 9/1999 Tamura et al. .............. 348/229

FOREIGN PATENT DOCUMENTS

JP             6-11754    *  1/1994  ............ G03B/7/28

* cited by examiner

Primary Examiner—John Mulcahy
(74) Attorney, Agent, or Firm—Snider & Associates; Ronald R. Snider

(57) ABSTRACT

In an electronic endoscope, and a memory which contains image pickup area information including size and light distribution characteristics are provided, and in a processor device to which this electronic endoscope is connected, a photometric part for measuring the light receiving state by using separated photometric areas, and a microcomputer are provided, and this microcomputer reads the above described image pickup area information on the electronic endoscope side, and sets a photometric areas ($E_A$ to $E_C$) whose size is approximately the same corresponding to the size of the image pickup area in the above described photometric part, and in the meantime, gives weightings A to C to each separated area of these photometric areas ($E_A$ to $E_C$). Consequently, even in the case where the sizes and the light distribution characteristics of the actual image pickup areas ($F_A$ to $F_C$) determined by the objective optical system are changed, it is possible to realize fine photometry and brightness control.

5 Claims, 7 Drawing Sheets

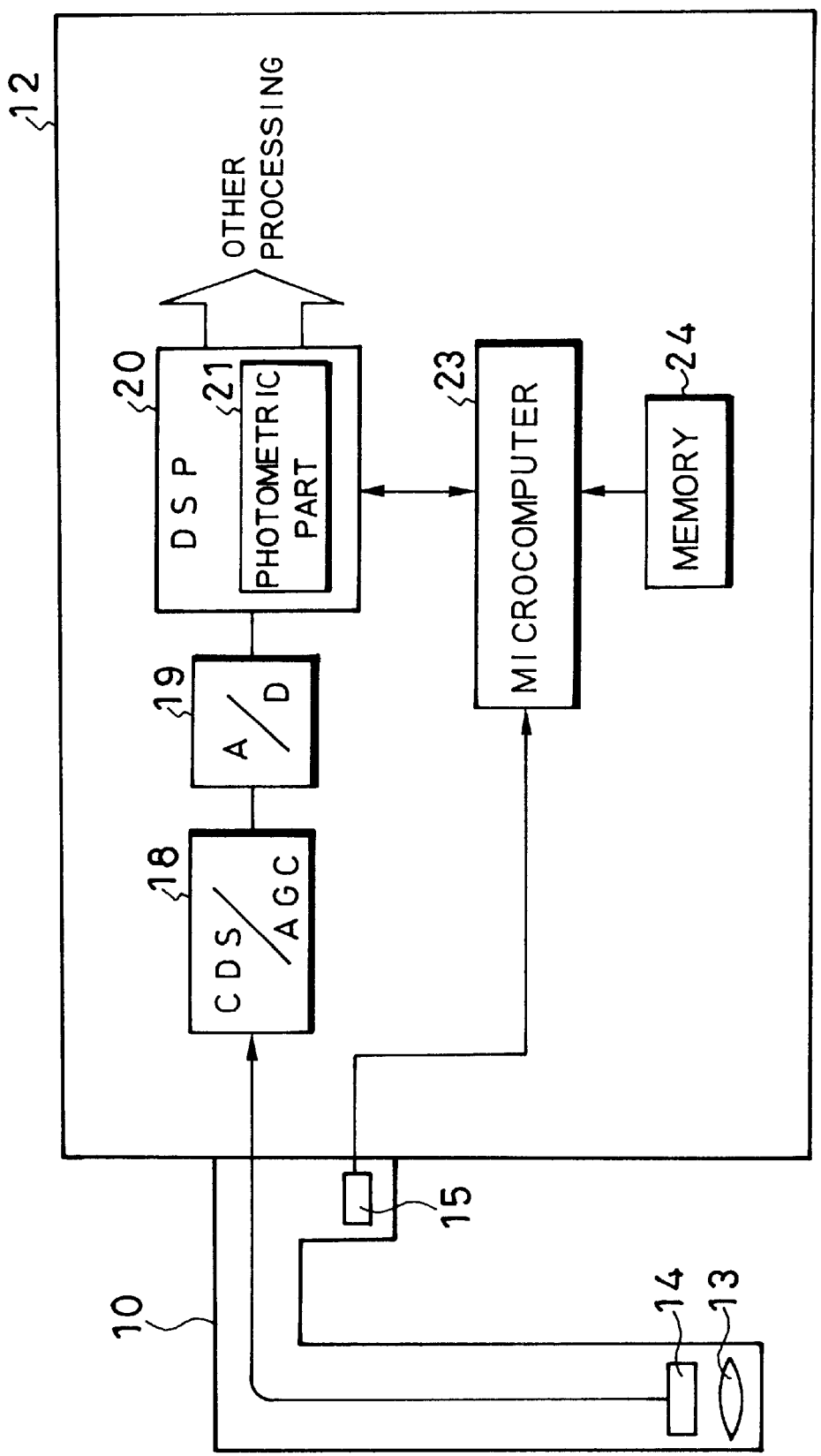

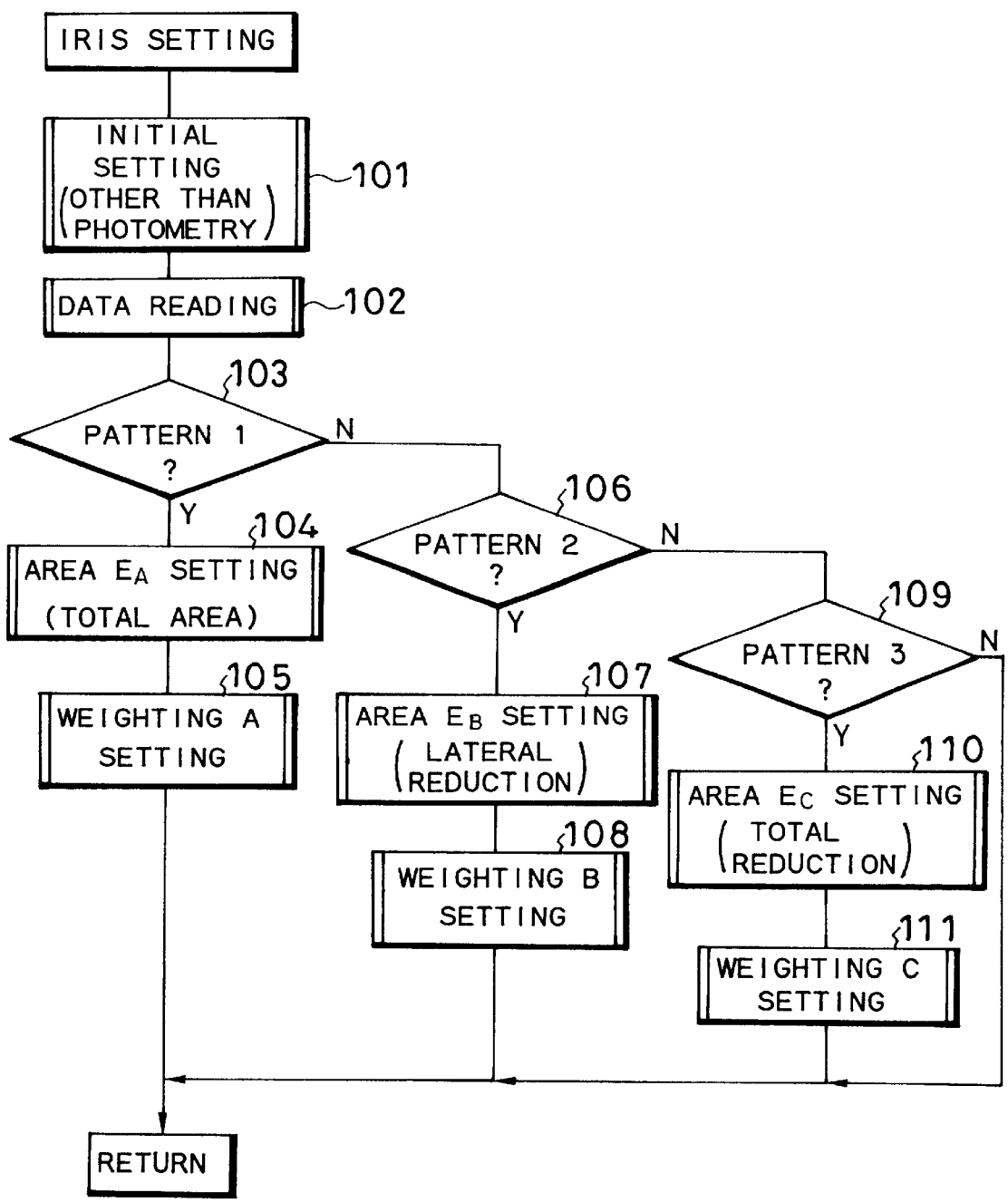

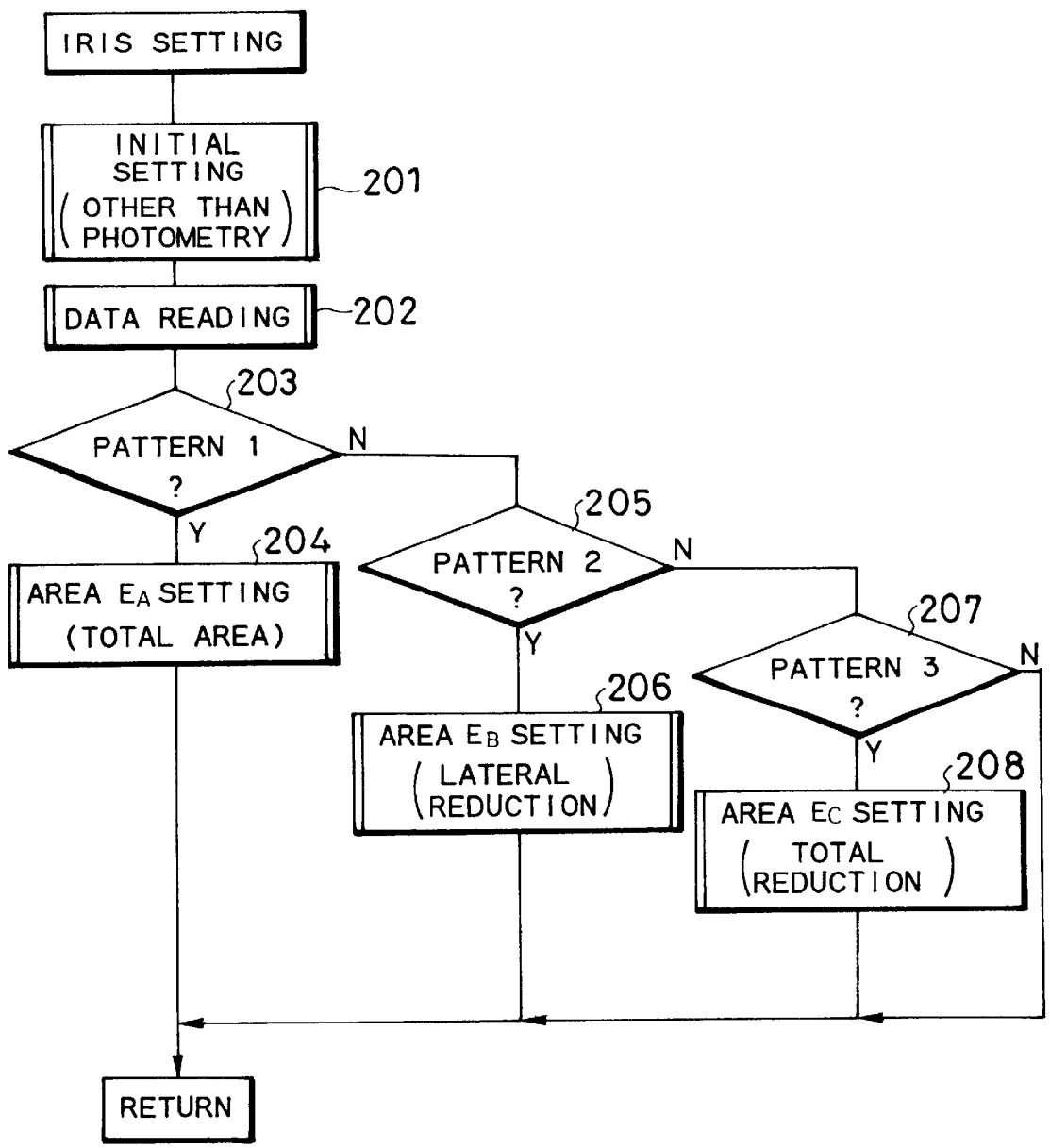

[WEIGHTING D]

PRIOR ART
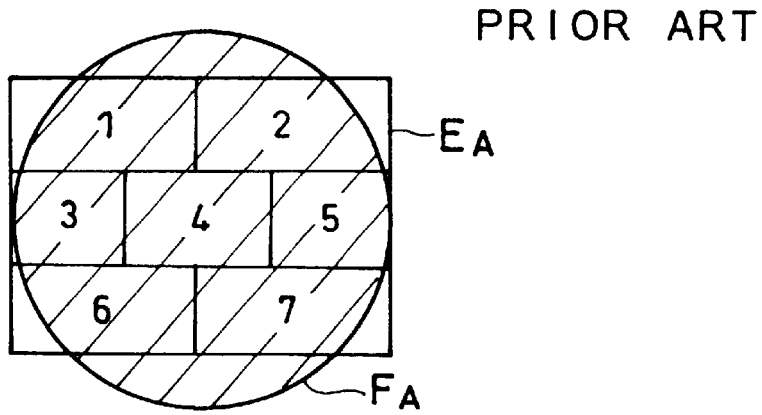
FIG.7 (A)
PRIOR ART
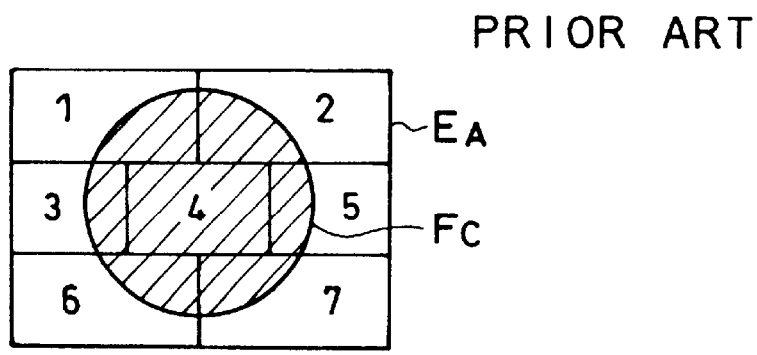
FIG.7 (B)
FIG. 8
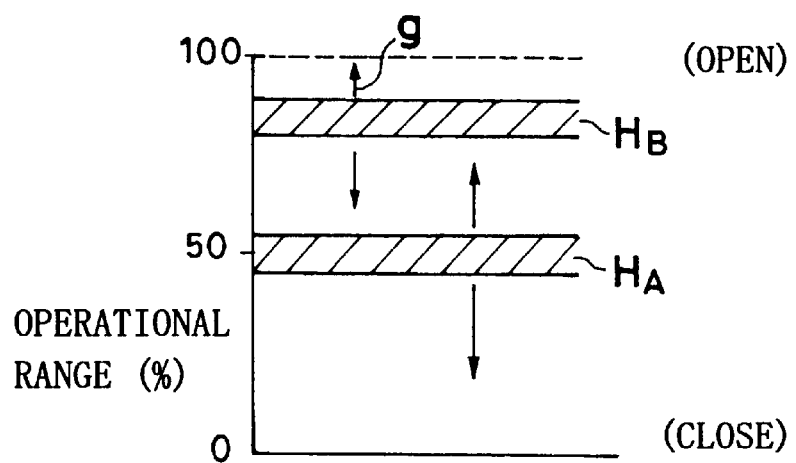

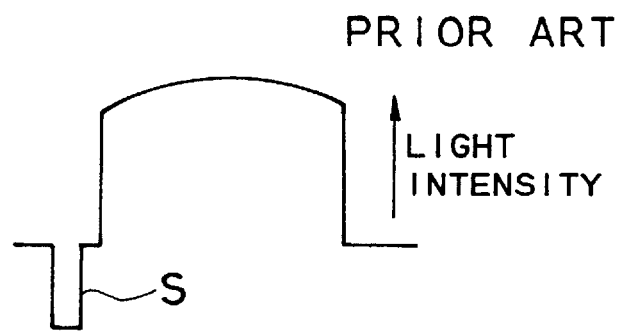
FIG.9(A) STANDARD SCOPE  PRIOR ART
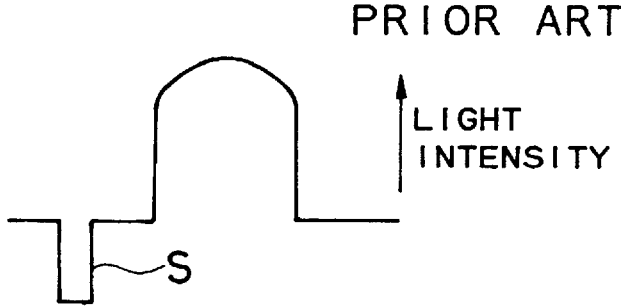
FIG.9(B) NARROW ANGLE SCOPE  PRIOR ART

US 6,475,141 B2

ELECTRONIC ENDOSCOPE DEVICE USING SEPARATED AREA PHOTOMETRY

BACKGROUND OF THE INVENTION

This application claims the priority of Japanese Patent Applications Nos. 2000-196394 and 2000-196395 filed on Jun. 29, 2000 which are incorporated herein by reference.

1. Field of the Invention

The present invention relates to an electronic endoscope device and particularly relates to a circuit configuration of measuring a light receiving state of an image pickup device in a separation photometric area set on an image pickup surface for controlling brightness of an image.

2. Description of the Prior Art

The electronic endoscope device displays an image of an observed object on a monitor by applying signal-processing with a processor device or the like to a picked-up image signal obtained by a solid image pickup device [CCD (Charge Coupled Device) provided in an electronic endoscope. Then, in this electronic endoscope device, the light receiving state in the above described CCD is measured, and the control for making the brightness of the image of the observed object displayed on the above described monitor fine is performed.

In FIG. 7(A), a conventional separated photometric area set on the image pickup surface of the CCD is shown. As shown in the figure, this square photometric area $E_A$ has one to seven separated areas on the image pickup surface, and to this photometric area $E_A$, the actual image pickup area (circular oblique hatching part) that is the luminous flux range of the image formation face of the objective optical system is $F_A$. In this photometric area $E_A$, the light receiving amount (luminance) of each of the separated areas 1 to 7 is detected, and for example, the central area 4 has a weighting factor of 2, the left and right areas 3 and 5 thereof have a weighting factor of 1.5, and the upper and lower areas 1, 2, 6, and 7 have a weighting factor of 1, and by multiplying each light receiving amount by the above described weighting factor, the total light receiving state (brightness) of the photometric area $E_A$ is determined.

Then, on the basis of this light receiving data of the photometric area $E_A$, in the electronic endoscope device, the iris control is performed in the light source device, or the electronic shutter control is performed in the above described CCD. That is, in the iris control circuit of the light source device, the diaphragm opening amount is controlled on the basis of the above described light receiving data, and by the output control of the light radiated to the observed object, an image with constant brightness can be obtained. Furthermore, in the electronic endoscope that performs the electronic shutter control, the charge storage time of the CCD is controlled on the basis of the above described receiving light data, and by controlling the incidence amount of the light of the image of the observed object (exposure value), an image with fine brightness can be obtained.

BRIEF SUMMARY OF THE INVENTION

Object of the Invention

However, the brightness control based on the above described conventional separated photometric area has had such a problem that the meaning and effect of performing the photometry for each separated area is diluted in the case where electronic endoscopes in which the size of the image pickup area is different are connected to the processor device or the like. That is, depending on the kind of the electronic endoscope, the actual image pickup area (image formation face luminous flux range) set by the objective optical system at the tip thereof is different, and as shown in FIG. 7(B), for example, there is a case where an image pickup area with a small $F_C$ is set (narrow angle scope), and even in the case where such an endoscope is connected, the photometric area set on the processor device side is $E_A$. As a result of this, as understood from FIG. 7(B), in the total photometry, the contribution of the light receiving amount of the central area 4 becomes larger than those of the peripheral areas 1 to 3, 5 to 7, and in the case where a projection or a depression exists at the central part, the peripheral part may become dark or the peripheral part may become too bright.

Furthermore, as shown in FIG. 7B, there is such a problem that when the actual image pickup area $F_C$ becomes smaller than the case of $F_A$ in FIG. 7A, the operational range of the diaphragm member thereof is narrowed in the iris control of the light source device or the like. That is, as shown in FIG. 8, in the iris control, it is preferable that the operational position of middle brightness is set at the central position $H_A$ of the diaphragm member movable range, and that the diaphragm member can be moved in the closing direction and opening direction from this position $H_A$, but when the total light receiving amount in the photometry is decreased, the above described operational position of middle brightness shifts to $H_B$. As a result of this, as shown in the figure, the operational range g in the direction of opening the diaphragm member is narrowed, so that fine light volume control cannot be performed.

Furthermore, in the electronic endoscope device, the light guided by a light guide is radiated to the observed object, and the reflected light thereof is incident on the image pickup surface of the image pickup device through the objective optical system, but the light distribution characteristic (light intensity distribution) caught by this image pickup surface (or the image pickup area) is different in the size of the above described actually set image pickup area, and there is such a problem that the light receiving amount measured in each of the separated areas 1 to 7 becomes unequal because of this difference in the light distribution characteristic.

FIGS. 9(A), 9(B) show the light distribution characteristics in the horizontal direction in the image pickup areas of FIGS. 7(A), 7(B), and FIG. 9(A) shows the light distribution characteristic of the image pickup area $F_A$ in FIG. 7(A) (standard scope), and FIG. 9(B) shows the light distribution characteristic of the image pickup area $F_C$ in FIG. 7(B) (narrow angle scope). S in FIGS. 9(A), 9(B) is a horizontal synchronous signal, and this light distribution characteristic shows the light intensity distribution along the horizontal scanning line. In the case of the standard scope, as shown in FIG. 9(A), a comparatively smooth light intensity distribution is made, but in the case of the narrow angle scope, as shown in FIG. 9(B), the light distribution characteristic is made such that the light intensity at the central part is high and it suddenly rises. Such a light distribution characteristic is similar in the directions of all orientations of the image pickup area $F_A$, and because of this difference in the light distribution characteristics, a difference is caused in the light receiving amounts of the central part 4 and the peripheral areas 1 to 3, 5 to 7.

The present invention is made in view of the above described problems, and it is an object thereof to provide an electronic endoscope device, wherein it is possible to perform the brightness control satisfactorily by equalizing the photometric conditions of the separated photometric areas, and furthermore, the operational range in the iris control or the like is also not narrowed, even in the case where the actual image pickup area or the light distribution characteristic thereof changes.

SUMMARY OF THE INVENTION

In order to attain the above described objects, the present invention comprises: various kinds of electronic endoscopes to which an objective optical system and an image pickup device are provided; a main unit which is arranged so that these electronic endoscopes can freely be connected, and which controls brightness of an image based on the light receiving state of the above described image pickup device; a photometric circuit which is provided to this main unit, and which measures the light receiving state of the above described image pickup device by the photometric area having a plurality of separated areas set in the image pickup surface of the above described image pickup device; and a determination circuit which gives a different weighting to the measured value of the separated area in the above described photometric area according to the light distribution characteristic of the image pickup area of the above described image pickup device, and which determines the brightness of an image.

The weighting in the above described determination circuit can be given considering the area ratio of each separated area of the above described photometric area.

It is possible that the image pickup area information including the above described light distribution characteristic is given to the above described electronic endoscope side, and that this image pickup area information is read on the above described main unit side, and that the above described weighting corresponding to this is set.

According to the above described configuration of the present invention, for example, a processor device on the main unit reads the image pickup area information (including size and light distribution characteristics) from the electronic endoscope side, and gives weighting to each separated area of the photometric area according to the light distribution characteristic of the actual image pickup area set on the image pickup surface of the image pickup device. It is preferable to set this weighting not only by considering the light distribution characteristic but also by considering the change of the area ratio of the image pickup area whose size is changed to the photometric area (change for each separated area). Consequently, even if electronic endoscopes different in light distribution characteristics or sizes of the image pickup area are connected to the processor device, non-uniformity of the photometric condition of the central area and the peripheral areas in the photometric area is canceled, and an image with a fine brightness can be formed.

Furthermore, another invention comprises: the above described various kinds of electronic endoscopes; the above described main body; a photometric circuit which is provided on the main body side, and in which various kinds of photometric areas having a plurality of separated areas and a different total size (area) are arranged to be able to be set in an image pickup surface of the above described image pickup device, and which measures the light receiving state of the above described image pickup device by the above described selected and set photometric area; and a control circuit which selects a photometric area in the above described photometric circuit according to the size of an image pickup area of the above described image pickup device determined by the objective optical system of the above described electronic endoscope.

In this case, the information of the above described image pickup area is also given to the above described electronic endoscope side, and on the above described main body side, this image pickup area information is read, and a photometric area corresponding to this is set.

According to this other invention, the ununiformity in the photometric conditions is furthermore canceled, and in the meantime, it does not occur for the operational range of the diaphragm member to be narrowed in the light source iris control or the like.

BRIEF DESCRIPTION OF THE DRAWINGS

FIG. 1 is a circuit diagram showing the configuration of an electronic endoscope device according to a first embodiment of the present invention;

FIG. 3 is a flow chart showing the iris setting operation in the device of the first embodiment;

FIG. 4 is a flow chart showing another example of the above described iris setting operation;

FIG. 7(A) is an explanation figure showing a relation of the image pickup area and the photometric area set in the conventional device;

FIG. 7(B) is an explanation figure showing another relation of the image pickup area and the photometric area set in the conventional device;

FIG. 8 is a graph showing the operational state in the iris control of the conventional device;

FIG. 9(A) is an explanation figure showing the light distribution characteristic of the incident light to the image pickup surface of the image pickup device in the standard scope; and FIG. 9(B) is an explanation figure showing the light distribution characteristic of the incident light to the image pickup surface of the image pickup device in the narrow angle scope.

DETAILED DESCRIPTION OF THE PREFERRED EMBODIMENTS

Figure 2A:
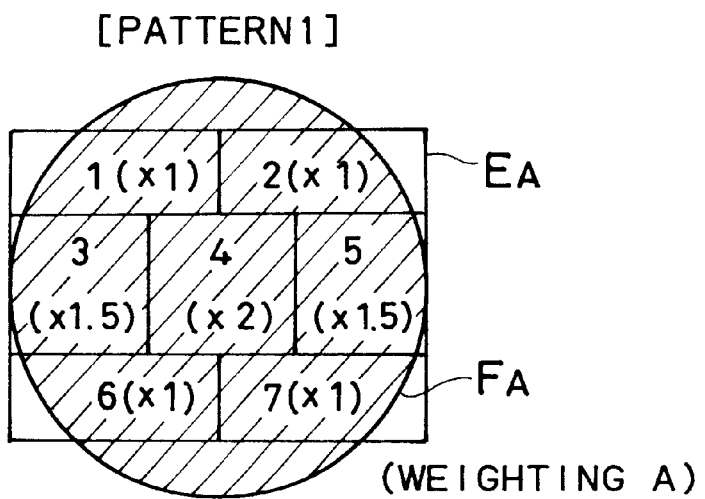
FIG. 2(A) is an explanation figure showing the standard pattern 1 of the image pickup area and the photometric area set in the first embodiment.

In FIG. 1, the circuit configuration of an electronic endoscope device according to a first embodiment is shown, and in the above described device, various kinds of electronic endoscopes (scopes) 10 are detachably attached to a processor device 12 on the main unit (body) side. In FIG. 1, in the electronic endoscope 10, a CCD 14 that is an image pickup device is arranged through an objective optical system 13 at the tip part, and at the connector part or the like, a memory (EEPROM) 15 containing information on the size of the image pickup area is provided.

On the other hand, in the processor device 12, a CDS/AGC (Correlated Double Sampling/Automatic Gain Control) circuit 18 into which the output signal of the CCD 14 is inputted and which performs the correlated double sampling and the automatic gain control is provided, and at the rear stage of this CDS/AGC circuit 18, an A/D converter 19 and a DSP (Digital Signal Processor) 20 which applies various kinds of image processing to the video signal are connected. In this DSP 20, a photometric part (luminance information detecting part) 21 which measures the light receiving state (brightness, luminance of an image) by using an adding register or the like on the basis of the separated photometric areas is provided. Furthermore, in order to perform various kinds of controls including the control of this photometric part 21, a microcomputer 23 and a memory 24 which contains information for various kinds of controls including the photometric area pattern data and the weighting data, or the like are arranged.

Figure 2B:
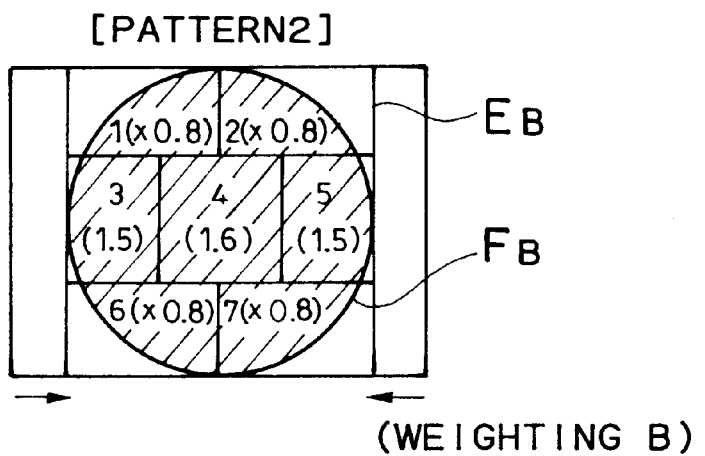
FIG. 2(B) is an explanation figure showing the reduction pattern 2 of the image pickup area and the photometric area set in the first embodiment.
Figure 2C:
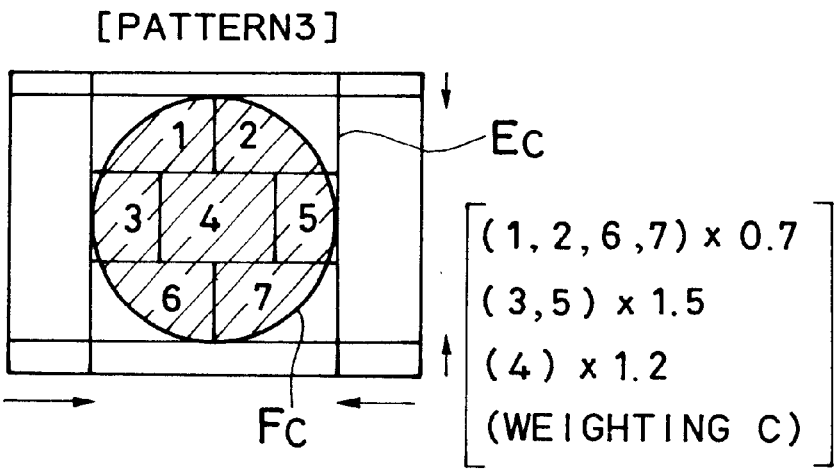
FIG. 2(C) is an explanation figure showing the reduction pattern 3 of the image pickup area and the photometric area set in the first embodiment.

Then, in the case of the above described example, it is possible to set a plurality of patterns of photometric areas $E_A$ to $E_C$ and weightings A to C that are shown in FIGS. 2(A) to 2(C) by controlling the above described microcomputer 23, and in the meantime, in this microcomputer 23, there is a determination circuit which gives a different weighting to the measured value of the separated area according to the light distribution characteristic of the image pickup area of the above described CCD 14, and which determines the brightness of the image. That is, FIG. 2(A) shows the standard pattern 1 that has existed in the past, and in the case of this pattern 1, to a circular image pickup area (slant hatching part) $F_A$ at the image formation position located by the objective optical system on the image pickup surface of the CCD 14, a square photometric area $E_A$ (having separated areas of 1 to 7) with which the left and right sides of the circumference thereof come into contact is set. Then, this standard pattern 1 has the light distribution characteristic (distribution) shown in FIG. 9(A), and considering this light distribution characteristic or the like, as the weighting A of the separated area in the photometric area $E_A$, a weighting factor of 1 is given to areas 1, 2, 6, 7, and a weighting factor of 1.5 is given to areas 3, 5, and a weighting factor of 2 is given to the central area 4.

FIG. 2(B) shows the reduction pattern 2, and in the case of this pattern 2, to a circular image pickup area $F_B$ smaller than that in FIG. 2(A) located on the image pickup surface of the same CCD 14, a square photometric area $E_B$ whose lateral width is shortened to come into contact with the left and right sides of the circumference thereof is set. In this photometric area $E_B$, the lateral widths of all separated areas 1 to 7 including the central area 4 are reduced. Furthermore, according to the light distribution characteristic of this image pickup area $F_B$, as the weighting B of the separated area in the photometric area $E_B$, a weighting factor of 0.8 is given to areas 1, 2, 6, 7, and a weighting factor of 1.5 is given to areas 3, 5, and a weighting factor of 1.6 is given to the central area 4.

FIG. 2(C) shows the reduction pattern 3, and in the case of this pattern 3, to a circular image pickup area $F_C$ furthermore smaller than that in FIG. 2(B) located on the image pickup surface of the same CCD 14, a square photometric area $E_C$ that is totally reduced to come into contact with the upper, lower, left, and right sides of the circumference thereof is set, and in this case, the sizes of all separated areas 1 to 7 are reduced by the same ratio. Then, this reduction pattern 3 has the light distribution characteristic of FIG. 9(B), and according to this light distribution characteristic, as the weighting C of the separated area in the photometric area $E_C$, a weighting factor of 0.7 is given to areas 1, 2, 6, 7, and a weighting factor of 1.5 is given to areas 3, 5, and a weighting factor of 1.2 is given to the central area 4.

That is, in the case of the light distribution characteristic [FIGS. 9(A), 9(B)] caught on the image pickup surface, the light intensity at the central part becomes higher as the diameter of the image pickup areas $F_A$ to $F_C$ becomes smaller, and therefore, the weighting of the central area 4 set in each of the photometric areas $E_A$ to $E_C$ is made smaller than those of the peripheral areas 1 to 3, 5 to 7. Then, the weightings B, C of the above described respective photometric areas $E_B$, $E_C$ are determined by considering the change of the area ratio of each of the separated areas 1 to 7 to the image pickup areas ($F_A$ to $F_C$) therein. Furthermore, the separation patterns (1 to 7) of these photometric areas $E_A$ to $E_C$ are not limited to this example, but various patterns can be applied.

The area configuration data and the weighting data of the above described photometric areas $E_A$ to $E_C$ are stored in the memory 24 or the like, and the microcomputer 23 reads the above described area configuration data out of this memory 24, and by specifying the address for each picture element unit of the CCD 14, the photometric area selected by the photometric part 21 is set. Consequently, the photometric part 21 calculates the light receiving amount for each picture element unit of the specified area for each of the separated areas (1 to 7), for example, by the additional averaging. Furthermore, the microcomputer 23 reads out the above described weighting data, and multiplies the above described calculated value by the weighting factor, and determines the total light receiving state on the basis of this.

Furthermore, in this electronic endoscope device, a light source part (device) which performs the variable control of the lamp light volume with a diaphragm member is provided, or an electronic shutter circuit which controls the charge storage time of the above described CCD 14 as the electronic shutter time, or the like is provided, which is not shown in the figure, and the control signal for controlling the brightness on the basis of the light receiving state obtained by the above described microcomputer is supplied to the above described light source part or electronic shutter circuit.

Figure 5:
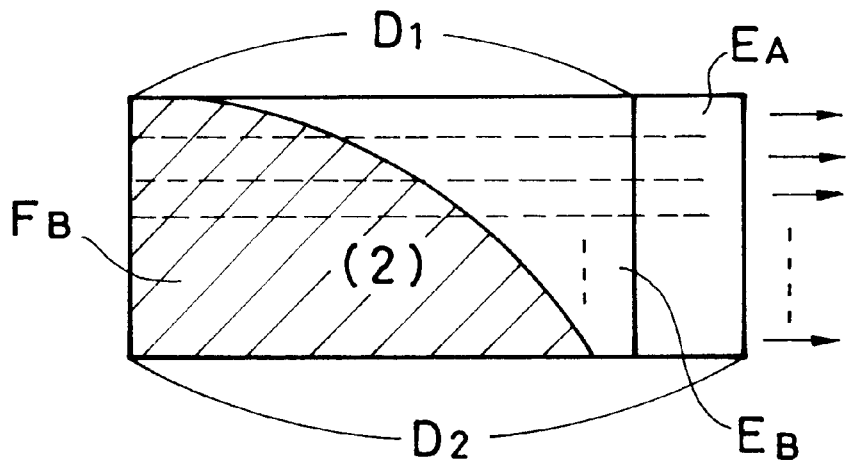
FIG. 5 is an explanation figure showing the comparison of the photometric area (separated area 2) between the reduction pattern (2) set in the first embodiment and the prior art.

The first embodiment is composed like the above description, and the action thereof will be described by referring to FIG. 3 and FIG. 5. In FIG. 3, in the iris setting routine, first, at Step 101, the initial setting other than the photometry is performed, and at the next Step 102, the image pickup area information (for example, pattern information) is read in from the memory 15 on the electronic endoscope 10 side. At the next Step 103, it is determined whether this image pickup area information is the standard pattern 1 or not, and when the determination is YES, the photometric area $E_A$ is set at Step 104, and the weighting A is given at the next Step 105. That is, the photometry is performed by the photometric area $E_A$ corresponding to the size of the image pickup area $F_A$ shown in FIG. 2(A).

On the other hand, when the determination is NO at Step 103, it is determined at Step 106 whether the image pickup area information is the reduction pattern 2 or not, and when the determination is YES, the photometric area $E_B$ is set at Step 107, and the weighting B is given at the next Step 108. That is, the photometry is performed by the photometric area $E_B$ corresponding to the size of the image pickup area $F_B$ shown in FIG. 2B. Furthermore, when the determination is NO at the above described Step 106, it is determined at Step 109 whether the image pickup area information is the reduction pattern 3 or not, and when the determination is YES, the photometric area $E_C$ is set at Step 110, and the weighting C is given at the next Step 111.

Then, in the photometric part 21 in FIG. 1, the photometry is performed by the photometric areas $E_A$ to $E_C$ corresponding to the sizes of the image pickup areas $F_A$ to $F_C$ shown in FIGS. 2(A) to 2(C). In FIG. 5, the separated area 2 of the above described photometric area $E_B$ is shown, and the photometry of this photometric area $E_B$ is performed such that the light receiving amounts for each picture element unit of the horizontal line with a length of $D_1$ are added by an adding register or the like in turn from the upper side to the lower side, and the additional average is calculated by an answering register or the like. On the other hand, in the prior art, the photometric area $E_A$ is set to the image pickup area $F_B$, and therefore, the light receiving amounts of the horizontal line with a length of $D_2$ are calculated by the additional averaging similarly to the above description from the upper side to the lower side. Accordingly, the photometric area $E_B$ of the above described example comes near the size of the image pickup area $F_B$ when compared with the conventional one ($E_A$), and the balance of the photometric value between the central area and the peripheral areas becomes similar to that of the above described standard pattern 1, and the result of the separated area photometry becomes approximately uniform.

After that, the measured value of each of the separated areas 1 to 7 optically measured at the above described photometric areas $E_A$ to $E_C$ is multiplied by each factor of the above described weightings A to C by the microcomputer 23, and the total light receiving state, that is, the brightness of the image is determined, and according to this determination output of brightness, the iris control or the electronic shutter control is performed.

In FIG. 4, an operation in the case where no weighting is given according to the above described light distribution characteristic is shown, and in this case, the selection of a photometric area suited to the size of the image pickup area of the image pickup device is merely performed.

Figure 6:
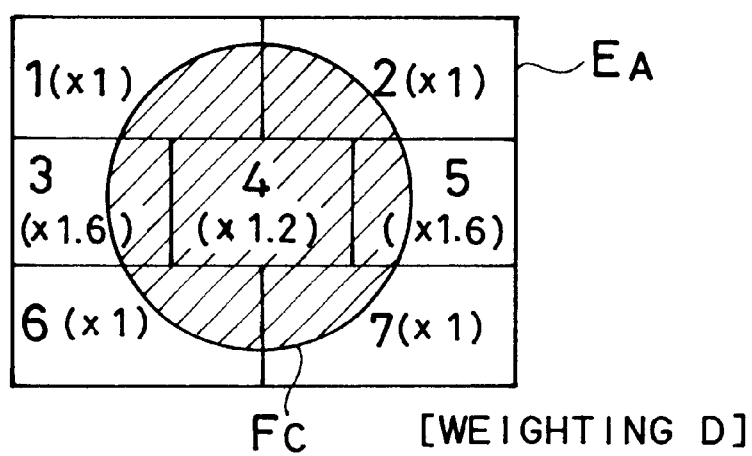
FIG. 6 is an explanation figure showing the image pickup area and the photometric area set in the second embodiment.

In FIG. 6, the configuration of the second embodiment is shown, and this second embodiment is made so that the size of the photometric area is not changed. In the case of this second embodiment, even if the size of the image pickup area is changed like $F_A$ to $F_C$ as mentioned above, the same photometric area $E_A$ as the standard pattern 1 is set at all times, and furthermore, the weighting is set considering the light distribution characteristic, and the ratio of the separated area to the image pickup areas ($F_A$ to $F_C$) whose sizes are changed therein.

In the case of FIG. 6, the weighting D at the time of the image pickup area $F_C$ is shown, and for example, a weighting factor of 1 is given to areas 1, 2, 6, 7, and a weighting factor of 1.6 is given to areas 3, 5, and a weighting factor of 1.2 is given to the central area 4. Consequently, even in the case of the reduced image pickup area $F_C$, the photometric conditions of the central area 4 and the peripheral areas 1 to 3, 5 to 7 become similar to those of other image pickup areas $F_A$, $F_B$, and a fine photometric result can be obtained.

Furthermore, in the lateral width reduction pattern 2 and the total reduction pattern 3 of the above described embodiments, a plurality of more minute patterns can be set. And, in the above described embodiment, information transmitting means of the image pickup area information (size, light distribution characteristics) given to the electronic endoscope 10 side may be structural means which can determine when the connector is connected, or it may also be means which determines directly the size of the image pickup area from the image data inputted in the processor device 12.

As described above, according to each embodiment, even in the case where the actual image pickup area is changed and light distribution characteristics are changed, it is possible to equalize the photometric conditions of the separated photometric areas and to perform the brightness control finely. Furthermore, in the above described photometric circuit, it is made possible to select and set a plurality of photometric areas whose sizes are different according to the size of the image pickup area, and therefore, it is possible to furthermore equalize the photometric conditions of the separated photometric areas, and furthermore, it becomes possible to form an image with a fine brightness, without narrowing the operational range of the diaphragm member at the time of the iris control.

What is claimed is:

1. An electronic endoscope device, comprising;
    various kinds of electronic endosoopes to which an objective optical system and an image pickup device are provided;
    a main unit which is arranged so that the electronic endoscopes can freely be connected, and which controls brightness of an image based on a light receiving state of said image pickup device;
    a photometric circuit which is provided on the main unit side, and which measures the light receiving state of said image pickup device by a photometric area having a plurality of separated areas set In an image pickup surface of said image pickup device; and
    a determination circuit which gives a different weighting to a measured value of the separated area in said photometric area according to light distribution characteristics of an image pickup area of said Image pickup device, and which determines brightness of an image.

2. The electronic endoscope device according to said claim 1, wherein weighting of said determination circuit is given considering the area ratio of each separated area of said photometric area.

3. The electronic endoscope device according to said claim 1, wherein image pickup area information including said light distribution characteristics is given to said electronic endoscope side, and the image pickup area information is read on said main unit side, and said weighting corresponding thereto is set.

4. An electronic endoscope device comprising:
    various kinds of electronic endoscopes to which an objective optical system and an image pickup device are provided: and
    a main body which is arranged such that the electronic endoscopes are freely connected thereto, and which controls brightness of an image on the basis of a light receiving state of said image pickup device,
    wherein said main body further comprises:
        a photometric circuit in which various kinds of photometric areas having a plurality of separated areas and a different total size are arranged to be able to be set in an image pickup surface of said image pickup device, and which measures the light receiving state of said image pickup device by said selected and set photometric area; and
        a control circuit which selects a photometric area in said photometric circuit according to the size of an image pickup area of said image pickup device determined by the objective optical system of said electronic endoscope.

5. The electronic endoscope device according to claim 4, wherein information of said image pickup area is given to said electronic endoscope side, and the information of the image pickup area is read on said main body side, and a photometric area corresponding thereto is set.

* * * * *

UNITED STATES PATENT AND TRADEMARK OFFICE
CERTIFICATE OF CORRECTION

PATENT NO. : 6,475,141 B2
DATED : November 5, 2002
INVENTOR(S) : Kazunori Abe

It is certified that error appears in the above-identified patent and that said Letters Patent is hereby corrected as shown below:

<u>Column 8,</u>
Line 12, delete "comprising;" and substitute therefore -- comprising: --
Line 23, delete "In" and substitute therefore -- in --
Line 28, delete "Image" and substitute therefore -- image --
Line 43, delete "provided:" and substitute therefore -- provided; --

Signed and Sealed this

Twenty-ninth Day of April, 2003

JAMES E. ROGAN
*Director of the United States Patent and Trademark Office*